(12) United States Patent
Devengenzo et al.

(10) Patent No.: US 12,274,521 B2
(45) Date of Patent: Apr. 15, 2025

(54) ROBOTIC ARM HAVING AN EXTENDABLE PRISMATIC LINK

(71) Applicant: Verb Surgical Inc., Santa Clara, CA (US)

(72) Inventors: Roman Devengenzo, San Jose, CA (US); Pablo Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 281 days.

(21) Appl. No.: 18/081,506

(22) Filed: Dec. 14, 2022

(65) Prior Publication Data

US 2023/0116397 A1 Apr. 13, 2023

Related U.S. Application Data

(62) Division of application No. 16/525,427, filed on Jul. 29, 2019, now Pat. No. 11,553,973.

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/25* (2016.02); *A61B 34/30* (2016.02); *B25J 9/0027* (2013.01);
(Continued)

(58) Field of Classification Search
CPC ................... A61B 34/35; A61B 34/30; A61B 2017/00477; B25J 9/0027; B25J 9/0039; B25J 9/06; B25J 18/02
See application file for complete search history.

(56) References Cited

U.S. PATENT DOCUMENTS

| 5,397,323 A | 3/1995 | Taylor et al. |
| 5,511,147 A | 4/1996 | Abdel-Malek |

(Continued)

FOREIGN PATENT DOCUMENTS

| JP | 06-261911 A | 9/1994 |
| JP | 2010-221043 A | 10/2010 |

(Continued)

OTHER PUBLICATIONS

Behrens et al., "Kinematics Analysis of A 3-DOF Joint For A Novel Hyper-Redundant Robot Arm", 2011 IEEE International Conference on Robotics and Automation, May 9, 2011-May 13, 2011, pp. 3224-3229, doi: 10.1109/ICRA.2011.5979897.

(Continued)

*Primary Examiner* — Thomas McEvoy
(74) *Attorney, Agent, or Firm* — Aikin & Gallant, LLP

(57) ABSTRACT

Robotic arms and surgical robotic systems incorporating such arms are described. A robotic arm includes a roll joint connected to a prismatic link by a pitch joint and a tool drive connected to the prismatic link by another pitch joint. The prismatic link includes several prismatic sublinks that are connected by a prismatic joint. A surgical tool supported by the tool drive can insert into a patient along an insertion axis through a remote center of motion of the robotic arm. Movement of the robotic arm can be controlled to telescopically move the prismatic sublinks relative to each other by the prismatic joint while maintaining the remote center of motion fixed. Other embodiments are also described and claimed.

7 Claims, 9 Drawing Sheets

(51) Int. Cl.
- *A61B 34/30* (2016.01)
- *B25J 9/00* (2006.01)
- *A61B 17/00* (2006.01)
- *A61B 34/20* (2016.01)

(52) U.S. Cl.
CPC ............ *A61B 2017/00199* (2013.01); *A61B 2017/00477* (2013.01); *A61B 2017/00973* (2013.01); *A61B 34/20* (2016.02); *B25J 9/0039* (2013.01)

(56) References Cited

U.S. PATENT DOCUMENTS

| | | |
|---|---|---|
| 6,277,030 B1 | 8/2001 | Baynton et al. |
| 6,451,027 B1 | 9/2002 | Cooper et al. |
| 6,723,106 B1 | 4/2004 | Charles et al. |
| 8,506,555 B2 | 8/2013 | Ruiz Morales |
| 9,295,524 B2 | 3/2016 | Schena et al. |
| 9,339,344 B2 | 5/2016 | Schena et al. |
| 9,358,682 B2 | 6/2016 | Ruiz Morales |
| 9,415,510 B2 | 8/2016 | Hourtash et al. |
| 2008/0282821 A1 | 11/2008 | Tokumitsu |
| 2012/0024091 A1 | 2/2012 | Kawabuchi et al. |
| 2012/0132018 A1 | 5/2012 | Tang et al. |
| 2013/0144307 A1 | 6/2013 | Jeong et al. |
| 2014/0163581 A1 | 6/2014 | Devengenzo et al. |
| 2014/0276951 A1 | 9/2014 | Hourtash et al. |
| 2015/0157410 A1 | 6/2015 | Kilroy et al. |
| 2019/0000576 A1 | 1/2019 | Mintz et al. |
| 2019/0069965 A1 | 3/2019 | Schena et al. |
| 2022/0233259 A1 | 7/2022 | Thompson et al. |

FOREIGN PATENT DOCUMENTS

| | | |
|---|---|---|
| JP | 2018-061853 A | 4/2018 |
| JP | 2019-502474 A | 1/2019 |
| WO | 2017/002142 A1 | 1/2017 |
| WO | 2018/005750 A1 | 1/2018 |
| WO | 2019074670 A1 | 4/2019 |

OTHER PUBLICATIONS

International Search Report and Written Opinion for International Application No. PCT/US2019/044526, mailed Apr. 28, 2020, 14 pages.
Office Action received for Japanese Patent Application No. 2022-506162, mailed on Jun. 6, 2023, 15 pages (8 pages of English Translation and 7 pages of Original Document).
Supplementary European Search Report and Search Opinion received for EP Application No. 19939981.7, mailed on Jul. 24, 2023, 9 pages.
Non-Final Office Action received for U.S. Appl. No. 16/525,427, mailed on Mar. 11, 2022, 10 pages.
Notice of Allowance received for U.S. Appl. No. 16/525,427, mailed on Sep. 21, 2022, 7 pages.
Office Action received for Japanese Patent Application No. 2022-506162 , mailed on Dec. 12, 2023, 11 pages (5 pages of English Translation and 6 pages of Original Document).
Office Action received for Korean Patent Application No. 10-2022-7006374, mailed on May 22, 2024, 5 pages English translation only.
Final Rejection received for Korean Patent Application No. 10-2022-7006374, mailed on Dec. 2, 2024, 7 pages (4 pages of Original Document and 3 pages of English Translation).

ROBOTIC ARM HAVING AN EXTENDABLE PRISMATIC LINK

CROSS-REFERENCE TO RELATED APPLICATIONS

This patent application is a divisional of U.S. patent application Ser. No. 16/525,427 filed on Jul. 29, 2019, and this application is specifically incorporated by reference herein in its entirety.

BACKGROUND

Field

Embodiments related to robotic systems are disclosed. More particularly, embodiments related to surgical robotic systems and corresponding mechanical linkages are disclosed.

Background Information

Endoscopic surgery involves looking into a patient's body and performing surgery inside the body using endoscopes and other surgical tools. For example, laparoscopic surgery can use a laparascope to access and view an abdominal cavity. Endoscopic surgery can be performed using manual tools and/or a surgical robotic system having robotically-assisted tools.

A surgical robotic system may be remotely operated by a surgeon to control a robotically-assisted tool located at an operating table. The surgical tool can be inserted into an access point in a patient, such as an incision in an abdominal wall of the patient. The surgeon may use a computer console located in the operating room, or it may be located in a different city, to command a robot to manipulate the surgical tool. The robotically-controlled surgical tool can be mounted on a robotic arm and the commands can cause movement of the robotic arm to position the surgical tool within the patient while maintain the surgical tool at a remote center of motion, which is a fixed point in space about which the surgical tool pivots. The remote center of motion can be collocated with the access point in the patient. Accordingly, the surgical robotic system may be controlled by the remote surgeon to position the surgical tool within the patient by moving the robotic arm during a robotic surgery.

SUMMARY

Existing robotic arms used for positioning surgical tools while maintaining the tools at a remote center of motion are hardware-constrained. In other words, the robotic arms include links of fixed lengths that are constrained relative to each other to impose a predetermined motion. For example, a hardware-constrained robotic arm can include links arranged in a parallelogram such that movement of an input link, which can be driven by a single motor, causes a predetermined movement of several other passive links, which are connected to the input link by passive joints. One of the passive links can be an output link that is constrained to pivot about a remote center of motion collocated with an access point in a patient. The remote center of motion remains fixed in space regardless of the position of the parallelogram links. Hardware-constrained robotic arms require links of fixed lengths that tend to be long in order to achieve a desired range of motion relative to the patient. Several issues follow from the requirement for long, fixed-length links. First, hardware-constrained robotic arms sweep out large spatial volumes during surgery, which can inhibit access to the patient by the surgeon or support staff who must avoid being hit by the arms. Second, the long, fixed-length links are large, both visually and by volume and weight. Thus, inertial loads of the links can be large, which must be accommodated by the use of bulky and more expensive motors and joints. Third, the large size of the links makes the hardware-constrained linkage unsuitable for stowage under a surgical table. Instead, the robotic arms must be stored above or to the side of the operating table where precious operating room space must be shared with other surgical equipment and operators.

A robotic arm for positioning a surgical tool is provided that has a software-controlled robotic arm having several joints or links that are not hardware-constrained relative to each other. Each joint or link can be actively driven by one or more respective motors. One or more of the joints or links may include prismatic joints. Accordingly, the joint(s) or link(s) may be extendable and have variable lengths. The software-controlled robotic arm can occupy a smaller spatial envelope (in at least one configuration) as compared to a hardware-constrained robotic arm. Accordingly, the robotic arm can be collapsed or compacted for stowage under a surgical table in a stowed configuration, and can be expanded to an active configuration to move over the patient. The size and orientation of the robotic arm can be adjusted when in the active configuration to balance a risk of hitting another robotic arm or a surgeon with a need for a certain range of motion for a surgical operation.

In an embodiment, a robotic arm includes a roll joint that is rotatable about a roll axis and a tool drive configured to support a surgical tool and/or a tool guide. For example, the tool drive may be coupled to the tool guide can receive a shaft of the surgical tool along an insertion axis. The roll axis and the insertion axis intersect at a remote center of motion. The surgical tool and/or the tool guide extend along the insertion axis and are configured for insertion along the insertion axis into a patient through the remote center of motion. The robotic arm can include several joints connecting links that are movable to maintain the remote center of motion fixed. For example, an extendable prismatic link can connect to the roll joint and the tool drive at respective pitch joints. For example, the roll joint can be coupled to the prismatic link at a first pitch joint, and the tool drive can be coupled to the prismatic link at a second pitch joint. The tool drive can be coupled to the second pitch joint at a coupling position, which may be movable along the insertion axis. The extendable prismatic link can include several prismatic sublinks that are connected to each other by a prismatic joint and can slide relative to each other along a linear axis. A processor can control movement, e.g., rotation or sliding, of the joints or links of robotic arm to maintain the remote center of motion fixed as the surgical tool is pitched forward or backward to perform a surgical operation.

The robotic arm can include one or more actuators associated with the various joints connecting the links. For example, a first motor can drive the roll joint to rotate relative to the prismatic link about a first pitch axis. Similarly, a second motor can drive the tool drive to rotate relative to the prismatic link about a second pitch axis. Further, a third motor can drive the prismatic sublinks to slide relative to each other along a linear axis. The motors can be independently actuated to drive the links separately, and thus, the links are not motion-constrained with respect to each other. The first pitch axis, second pitch axis, and linear axis can be arranged in a manner that maintains the insertion axis and the roll axis in a same plane. For example, the first pitch axis can be parallel to the second pitch axis, and the linear axis can be orthogonal to both pitch axes. Accordingly, the linear axis, roll axis, and insertion axis can form a reference triangle having a vertex located at the remote center of motion. Actuating the various motors can change a shape of the reference triangle while maintaining the vertex at a location at the remote center of motion. As the geometry of robotic arm changes, the insertion axis can sweep through a working angle that defines a range of motion of the surgical tool tip within the patient.

The working angle can depend on a home configuration of the robotic arm. More particularly, the robotic arm can have several home configurations in which the roll axis is orthogonal to the insertion axis, e.g., when the reference triangle is a right triangle. Several home configurations exist because the prismatic joint can extend and the pitch joints can rotate to form different right triangles. For each home configuration, the working angle can differ based on a distance between the first pitch joint and the remote center of motion for that home configuration. For example, as the remote center of motion is moved farther from the first pitch joint connecting the roll joint to the prismatic link, the working angle may decrease. Adjustment of the working angle can be chosen by selecting an appropriate home configuration to balance a range of motion of the surgical tool within the patient against the desire to reduce the risk of collisions between the linkage and another linkage or an operator outside of the patient.

In an embodiment, a surgical robotic system includes a robotic arm mounted on an operating table. For example, the robotic arm can be mounted under the operating table. The prismatic joint of the robotic arm can be shortened, and the pitch joints can be rotated to fold the robotic arm into a stowage configuration. In the stowage configuration, the robotic arm has a smaller form factor than when the linkage is in an active configuration over the patient. For example, at least one link of the robotic arm can be shorter in the stowage configuration than in the active configuration. Accordingly, the robotic arm can be stowed under the operating table in the smaller form factor, even though it may not be possible to stow the linkage under the operating table when the prismatic link is extended to the active configuration.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
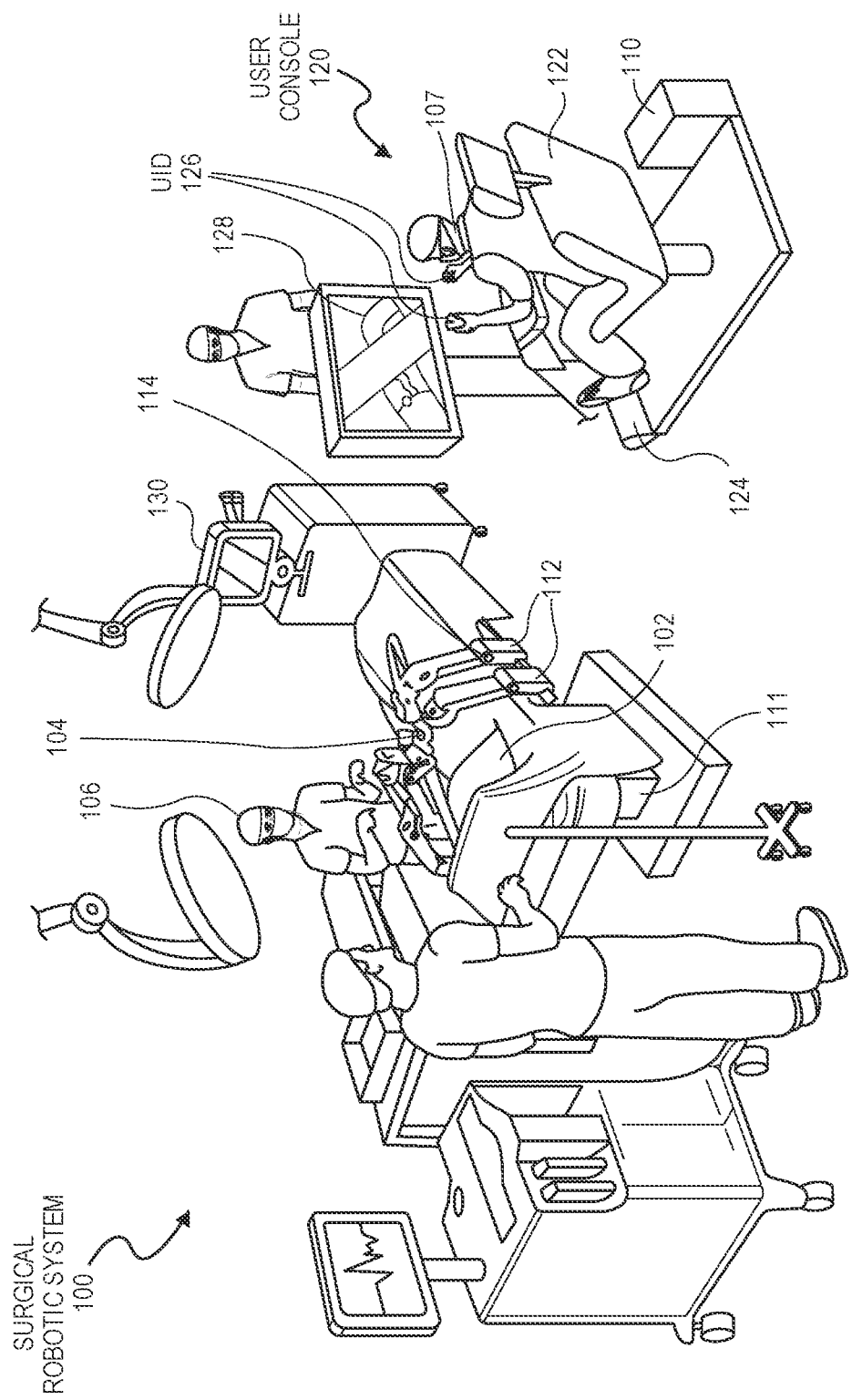
FIG. 1 is a pictorial view of an example surgical robotic system in an operating arena, in accordance with an embodiment.

Embodiments describe a mechanical linkage and robotic systems incorporating such linkages. The mechanical linkage can be a robotic arm and the robotic system can be a surgical robotic system that incorporates the robotic arm to position a surgical tool during a robotic surgery. The mechanical linkage may, however, be used in other robotic systems, such as for manufacturing or military applications, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from a mounting point. Similarly, "proximal" may indicate a location in a second direction opposite to the first direction, e.g., toward the mounting point. Such terms are provided to establish relative frames of reference, however, and are not intended to limit the use or orientation of a robotic arm to a specific configuration described in the various embodiments below.

In an aspect, a surgical robotic arm is capable of positioning and controlling a surgical tool or instrument during a surgery, such as a laparoscopic surgery. The surgical robotic arm may be software-controlled, as compared to hardware-constrained, and may include one or more joints or links that can independently vary their lengths and orientations based on computer-based control of respective actuators. For example, a motor can be controlled to rotate several links of the surgical robotic arm relative to each other, and another motor can be controlled to slide several sublinks of one of the links relative to each other. The motors can control an overall geometry of the robotic arm during surgery such that a surgical tool is maintained at a remote center of motion. The remote center of motion can coincide with an access point in a patient during a surgery. Before and after the surgery, the motors can drive the overall geometry to a stowed configuration in which the robotic arm is compact and can be stowed under an operating table that supports the patient.

Referring to FIG. 1, this is a pictorial view of an example robotic system in an operating arena. A surgical robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may be an end effector that is attached to a distal end of a surgical arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 is a grasper that can grasp tissue of patient 102. Surgical tool 104 may be controlled manually, by a bedside operator 106; or it may be controlled robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user interface devices, UIDS 126, and at least one user display 128 that is configured to display, for example, a view of the surgical site inside patient 102. In the example user console 120, remote operator 107 is sitting in seat 122 and viewing the user display 128 while manipulating a foot-operated control 124 and a handheld UID 126 in order to remotely control the arms 112 and surgical tools 104 (that are mounted on the distal ends of the arms 112). Foot-operated control(s) 124 can be foot pedals, such as seven pedals, that generate motion control signals when actuated. User console 120 may include one or more additional interface devices (FIG. 10), such as a keyboard or a joystick, to receive manual inputs to control operations of user console 120 or surgical robotic system 100.

In some variations, bedside operator 106 may also operate system 100 in an "over the bed" mode, in which bedside operator 106 (user) is now at a side of patient 102 and is simultaneously manipulating a robotically-driven tool (end effector attached to arm 112), e.g., with a handheld UID 126 held in one hand, and a manual laparoscopic tool. For example, the bedside operator's left hand may be manipulating the handheld UID 126 to control a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion to achieve anesthesia. Initial access to the surgical site may be performed manually while the arms of the robotic system 100 are in a stowed configuration, e.g., under platform 111, or withdrawn configuration (to facilitate access to the surgical site). Once access is completed, initial positioning or preparation of the robotic system including its arms 112 may be performed. Next, the surgery proceeds with the remote operator 107 at the user console 120 utilizing the foot-operated controls 124 and the UIDs 126 to manipulate the various end effectors and perhaps an imaging system, to perform the surgery. Manual assistance may also be provided at the procedure bed or table, by sterile-gowned bedside personnel, e.g., bedside operator 106 who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move a robot arm actuator 114 in robotic system 100. UID 126 may be communicatively coupled to the rest of robotic system 100, e.g., via a console computer system 110. UID 126 can generate spatial state signals corresponding to movement of UID 126, e.g., position and orientation of the handheld housing of the UID, and the spatial state signals may be input signals to control a motion of the robot arm actuator 114. Robotic system 100 may use control signals derived from the spatial state signals, to control proportional motion of actuator 114. In one embodiment, a console processor of console computer system 110 receives the spatial state signals and generates the corresponding control signals. Based on these control signals, which control how the actuator 114 is energized to move a segment or link of arm 112, the movement of a corresponding surgical tool 104 that is attached to the arm may mimic the movement of UID 126. Similarly, interaction between remote operator 107 and UID 126 can generate for example a grip control signal that causes a jaw of a grasper of surgical tool 104 to close and grip the tissue of patient 102.

Surgical robotic system 100 may include several UIDs 126, where respective control signals are generated for each UID that control the actuators and the surgical tool (end effector) of a respective arm 112. For example, remote operator 107 may move a first UID 126 to control the motion of actuator 114 that is in a left robotic arm, where the actuator responds by moving linkages, gears, etc., in that arm 112. Similarly, movement of a second UID 126 by remote operator 107 controls the motion of another actuator 114, which in turn moves other linkages, gears, etc., of the robotic system 100. Robotic system 100 may include a right arm 112 that is secured to the bed or table to the right side of the patient, and a left arm 112 that is at the left side of the patient. An actuator 114 may include one or more motors that are controlled so that they drive the rotation or linear movement of a joint of arm 112, to for example change, relative to the patient, an orientation of an endoscope or a grasper of the surgical tool that is attached to that arm. Motion of several actuators 114 in the same arm 112 can be controlled by the spatial state signals generated from a particular UID 126. UIDs 126 can also control motion of respective surgical tool graspers. For example, each UID 126 can generate a respective grip signal to control motion of an actuator, e.g., a linear actuator, that opens or closes jaws of the grasper at a distal end of the surgical tool to grip tissue within patient 102.

In some aspects, the communication between platform 111 and user console 120 may be through a control tower 130, which may translate user commands that are received from user console 120 (and more particularly from console computer system 110) into robotic control commands that are transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
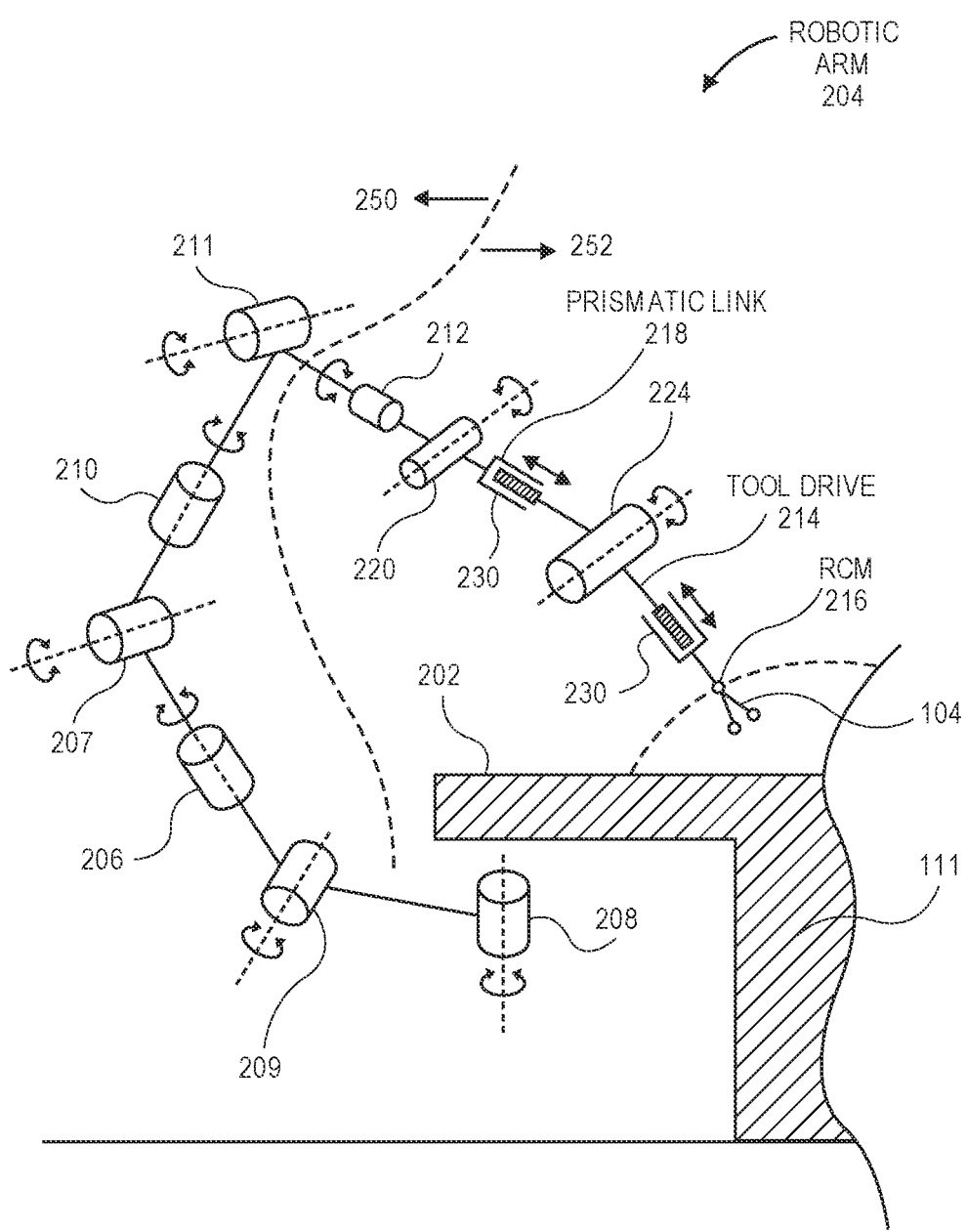
FIG. 2 is a schematic view of a surgical robotic system having a robotic arm, in accordance with an embodiment.

Referring to FIG. 2, a schematic view of a surgical robotic system having a robotic arm is shown in accordance with an embodiment. Surgical robotic system 100 can maintain a remote center of motion fixed, as described below. Surgical robotic system 100 can include surgical robotic arm 112 mounted on surgical robotic platform 111. Surgical robotic platform 111 can include several components, such as an operating table 202 on which patient 102 lies during the surgery, and a support column or legs that hold operating table 202 above the ground. Similarly, surgical robotic arm 112 can include several components, such as a robotic arm 204 having several joints or links, and several actuators, e.g., motors, that can drive the joints or links relative to each other. In FIG. 2, revolute joints have been represented as cylinders and links are shown having lines connecting the cylinders. In an embodiment, robotic arm 204 is mounted under operating table 202, and can be stowed under operating table 202 in a stowed configuration (not shown). Robotic arm 204 can be moved by actuators from the stowed configuration to an active configuration in which surgical tool 104 is positioned over operating table 202, as shown.

Surgical robotic arm 112 can be a multi-axis robotic manipulator capable of positioning and controlling surgical tool 104 during surgery. The axes of surgical robotic arm 112 represent degrees of freedom controlling an overall geometry of robotic arm 204. For example, a setup arm 250 having several linked joints can be attached to operating table 202, e.g., to an underside of operating table 202. The setup arm 250 can be coupled to operating table 202 by a table adapter joint 208 having one or more degrees of freedom. Table adapter joint 208 can be any combination of sub-joints, e.g., a pair of revolute joints, that allow movement of the setup arm 250 about several axes relative to operating table 202. Similarly, the setup arm 250 can include an adapter joint 209, which when combined with table adapter joint 208, provides one or more degrees of freedom of the setup arm 250 relative to the operating table 202. The setup arm 250 can include one or more additional joints, e.g., rolls joints such as joint 206 and/or joint 210 or pitch joints such as joint 207 and/or joint 211, that impart one or more degrees of freedom to interconnected arms. Each joint can allow rotation about a respective axis, hence the corresponding terms "pitch" and "roll." The linked arms of the setup arm 250, and any other links of robotic arm 204 between operating table 202 and a remote center of motion mechanism can position the remote center of motion mechanism in space with a predetermined degree of freedom. For example, the links between operating table 202 and a roll joint 212 of robotic arm 204 can combine to form a five degree-of-freedom arm, e.g., setup arm 250, that positions a proximal end of roll joint 212 in space.

The remote center of motion mechanism can include several joints or links. In an embodiment, roll joint 212 is a first joint in the remote center of motion mechanism. The remote center of motion mechanism can also be referred to as a spherical arm 252, and a proximal end of the spherical arm 252 can connect to a distal end of the setup arm 250. Similarly, a distal end of the spherical arm 252 can connect to a tool drive 214. The remote center of motion mechanism is configured to hold and orient surgical tool 104 (or tool drive 214 that holds surgical tool 104) at the remote center of motion 216 during surgery. Accordingly, the spherical arm 252 is essentially a portion of robotic arm 204 that defines the remote center of motion 216 about which surgical tool 104 pivots.

In addition to roll joint 212 and tool drive 214, the remote center of motion mechanism includes a prismatic link 218 connecting roll joint 212 to tool drive 214. More particularly, a distal end of roll joint 212 can connect to a proximal end of prismatic link 218. A first pitch joint 220 may also be coupled to roll joint 212 and prismatic link 218. For example, first pitch joint 220 may be intermediately between roll joint 212 and prismatic link 218. In an embodiment, a first motor is connected to roll joint 212 and prismatic link 218 to provide one or more degrees of freedom at first pitch joint 220. For example, prismatic link 218 can pivot relative to roll joint 212 about first pitch joint 220. Similarly, a distal end of prismatic link 218 can connect to tool drive 214 at a second pitch joint 224. A second motor can be connected to prismatic link 218 and tool drive 214 to provide one or more degrees of freedom at second pitch joint 224. For example, tool drive 214 can pivot relative to prismatic link 218 about second pitch joint 224.

One or more of the links forming the remote center of motion mechanism has a variable length. For example, link(s) of the remote center of motion mechanism can include sublinks connected to each other by a prismatic joint 230. The prismatic joint 230 allows sliding movement between the sublinks, and thus, an overall length of the link comprised of the sublinks can be increased or decreased. In an embodiment, prismatic link 218 of robotic arm 204 includes prismatic joint 230 between roll joint 212 and tool drive 214. For example, as described below, prismatic link 218 can have several prismatic sublinks coupled by prismatic joint 230, and a motor connected to the prismatic sublinks can slide the sublinks relative to each other to increase or decrease a length of prismatic link 218 and, consequently, a distance between tool drive 214 and roll joint 212.

Prismatic joints 230 can be incorporated into other components of surgical robotic arm 112. For example, tool drive 214 may include a prismatic joint 230 to allow surgical tool 104 to move linearly relative to an attachment point between tool drive 214 and second pitch joint 224. Prismatic joint 230 of tool drive 214 can be a telescoping body that can advance or retract relative to patient 102. The sliding movement can allow surgical tool 104 to insert into and retract from patient 102. Furthermore, all of the actuators of surgical robotic arm 112 can be controlled in coordination to maintain surgical tool 104 at remote center of motion 216.

Figure 3:
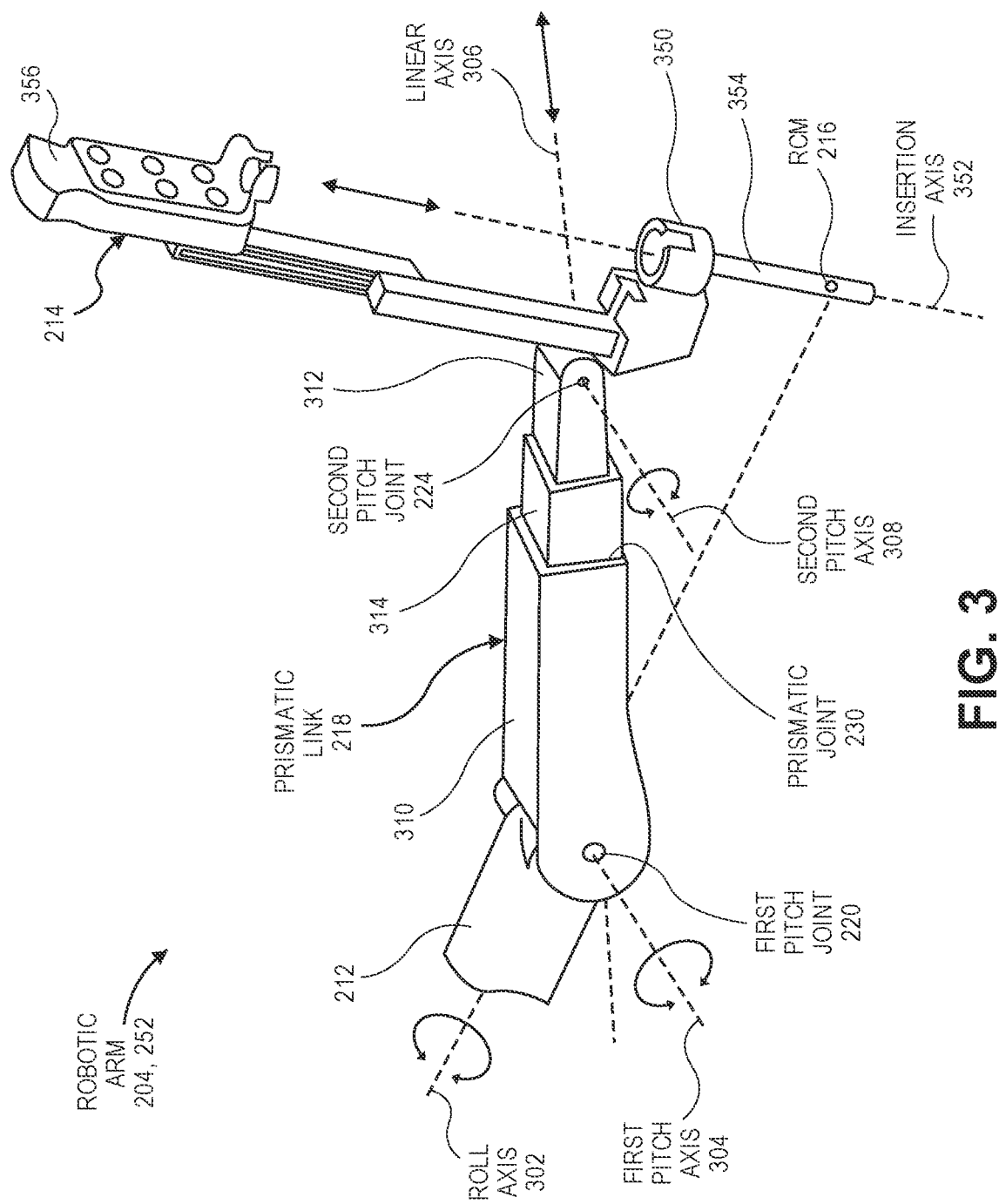
FIG. 3 is a perspective view of a robotic arm, in accordance with an embodiment.

Referring to FIG. 3, a perspective view of a robotic arm is shown in accordance with an embodiment. Robotic arm 204 can include the spherical arm 252. Robotic arm 204 can include roll joint 212 extending along a roll axis 302. Roll axis 302 is a geometric reference feature about which roll joint 212 may rotate. For example, a proximal end of roll joint 212 may attach to setup arm 250 at a revolute joint, e.g., joint 211. A motor can drive rotation of roll joint 212 at the revolute joint to cause a distal end of roll joint 212 to rotate about roll axis 302. Accordingly, roll joint 212 may provide at least one degree of freedom to robotic arm 204, e.g., rotation about roll axis 302.

Roll axis 302 can extend through the distal end of roll joint 212 where roll joint 212 connects to prismatic link 218 at first pitch joint 220. First pitch joint 220 can rotate about a first pitch axis 304. More particularly, the distal end of roll joint 212 can be connected to a proximal end of prismatic link 218 by first pitch joint 220, and a corresponding actuator can drive rotation of prismatic link 218 relative to roll joint 212 at first pitch joint 220. For example, a motor can be connected to roll joint 212 and prismatic link 218 at first pitch joint 220, and actuation of the motor can rotate prismatic link 218 relative to roll joint 212 about first pitch axis 304. Accordingly, first pitch joint 220 may provide at least one degree of freedom to robotic arm 204, e.g., rotation about first pitch axis 304.

Prismatic link 218 can extend along a linear axis 306 from the proximal end at first pitch joint 220 to a distal end at second pitch joint 224. Second pitch joint 224 can connect prismatic link 218 to tool drive 214. Second pitch joint 224 can rotate about a second pitch axis 308. More particularly, a corresponding actuator can drive rotation of prismatic link 218 relative to tool drive 214 at second pitch joint 224. For example, a motor can be connected to tool drive 214 and prismatic link 218 at second pitch joint 224, and actuation of the motor can rotate prismatic link 218 relative to tool drive 214 about second pitch axis 308. Accordingly, second pitch joint 224 may provide at least one degree of freedom to robotic arm 204, e.g., rotation about second pitch axis 308.

In addition to first pitch joint 220 and second pitch joint 224, prismatic link 218 may be associated with prismatic joint 230, which imparts an additional degree of freedom to robotic arm 204. Prismatic joint 230 can allow prismatic link 218 to extend and retract along linear axis 306. In an embodiment, prismatic link 218 includes a first prismatic sublink 310 having the proximal end of prismatic link 218. The proximal end of first prismatic sublink 310 can be connected to roll joint 212 by first pitch joint 220. Similarly, prismatic link 218 can include a second prismatic sublink 312 having the distal end of prismatic link 218. The distal end of second prismatic sublink 312 can be connected to tool drive 214 by second pitch joint 224. First prismatic sublink 310 may be connected to second prismatic sublink 312 directly or indirectly by prismatic joint 230.

Prismatic joint 230 of prismatic link 218 can include one or more stages. For example, first prismatic sublink 310 can have an elongated tubular construction, and an inner surface of the tubular wall of first prismatic sublink 310 may slide against an outer surface of second prismatic sublink 312. When the input sublink and the output sublink of prismatic link 218 are directly connected, e.g., when prismatic link 218 has only two segments, prismatic joint 230 may be a single-stage prismatic joint 230.

In an embodiment, prismatic link 218 is a telescoping structure having more than two segments. More particularly, prismatic link 218 can include first prismatic sublink 310, second prismatic sublink 312, and at least one additional prismatic sublink. The additional prismatic sublink link may be an intermediate prismatic sublink 314 connected to first prismatic sublink 310 and second prismatic sublink 312 by prismatic joint 230. More particularly, prismatic joint 230 can include a sliding contact between first prismatic sublink 310 and intermediate prismatic sublink 314, and a sliding contact between intermediate prismatic sublink 314 and second prismatic sublink 312. When the input sublink and the output sublink of prismatic link 218 are not directly connected, e.g., when prismatic link 218 has at least one intermediate prismatic sublink between first prismatic sublink 310 and second prismatic sublink 312, prismatic joint 230 may be a multi-stage prismatic joint 230.

Whether prismatic joint 230 is a single-stage or multi-stage prismatic joint, a distance between first pitch joint 220 and second pitch joint 224 can be increased by driving second prismatic sublink 312 away from first prismatic sublink 310, and the distance can be decreased by driving second prismatic sublink 312 toward first prismatic sublink 310. A corresponding actuator can drive translation of the prismatic sublinks, e.g., first prismatic sublink 310 and second prismatic sublink 312, relative to each other along linear axis 306. For example, a motor can be connected to first prismatic sublink 310 and second prismatic sublink 312, either directly or through intermediate prismatic sublink 314, to slide first prismatic sublink 310 relative to second prismatic sublink 312 along linear axis 306.

Extension and retraction of prismatic link 218 along linear axis 306 can change an overall size of robotic arm 204. For example, second prismatic sublink 312 can be driven toward first prismatic sublink 310 along linear axis 306 to decrease the length of prismatic link 218 until second pitch joint 224 is adjacent to a distal end of first prismatic sublink 310. In this state, prismatic link 218 would be at or near a minimum length. Accordingly, robotic arm 204 can be more compact in a state when second prismatic sublink 312 is retracted than in a state when second prismatic sublink 312 is extended. In an embodiment, robotic arm 204 is stowed under operating table 202 when prismatic link 218 is at or near the minimum length state. The variable length of extendable prismatic link 218 therefore imparts compactness to robotic arm 204, and allows robotic arm 204 to be stowed without taking up space above or to the side of operating table 202, when not in use.

It will be appreciated that a maximum length of prismatic link 218 can be increased by using more link segments. For example, increasing a number of stages in prismatic joint 230 can have a proportional increase in a range of motion of prismatic link 218 along linear axis 306. Increasing the number of stages, however, can increase the size, weight, and complexity of the system. It has been shown that a design may balance the arm reach required to perform a surgical operation against the ability to stow the compacted linkage under the operating table. In an embodiment, this balance is achieved by a prismatic joint 230 having two stages (with prismatic link 218 including three sublinks connected at two sliding points of contact) as shown in FIG. 3.

Prismatic link 218 can support tool drive 214, which can hold and move surgical tool 104. Tool drive 214 can also guide the movement of surgical tool 104 during the surgery. In an embodiment, tool drive 214 is configured to support surgical tool 104 (not shown in FIG. 3) and/or a tool guide 350. Surgical tool 104 and/or tool guide 350 can extend along an insertion axis 352. Surgical tool 104 and/or tool guide 350 can be configured for insertion along insertion axis 352 into patient 102 through remote center of motion 216. A component of tool guide 350, e.g., a guide tube 354, can receive and guide a feature of surgical tool 104, e.g., a distal shaft of surgical tool 104. For example, guide tube 354 can include a trocar having a lumen that is coaxial with the insertion axis 352, and thus, can receive the shaft of surgical tool 104 when the shaft is inserted into the lumen. Guide tube 354 can guide the tool feature into or through the access point in patient 102. Accordingly, insertion axis 352, the shaft of surgical tool 104, and the lumen of guide tube 354 can extend through remote center of motion 216.

In an embodiment, insertion axis 352 intersects roll axis 302 at remote center of motion 216. The intersection between insertion axis 352 and roll axis 302 is facilitated by the relative orientation of other reference geometry of the remote center of motion mechanism. For example, first pitch axis 304 can be parallel to second pitch axis 308. Accordingly, rotation of first pitch joint 220 and/or second pitch joint 224 can change a distance along roll axis 302 between first pitch axis 304 and insertion axis 352 without moving the axes out of plane. That is, the parallel pitch axes 304, 308 are orthogonal to a same plane within which axes 302, 352 are coplanar, and thus, rotation of the links about axes 304, 308 cause relative movement of axes 302, 352 within the same plane. Roll axis 302 and insertion axis 352 therefore remain coplanar during movement of the remote center of motion mechanism. Similarly, prismatic joint 230 can slide along linear axis 306, which may be orthogonal to first pitch axis 304 and second pitch axis 308. Orthogonality between linear axis 306 and the pitch axes allows insertion axis 352 to remain within the same plane as roll axis 302 even as the length of prismatic link 218 is changed from the stow configuration to the active configuration.

The relative position between robotic arm components and reference geometries can create a structure in which a reference triangle is formed by roll axis 302, linear axis 306, and insertion axis 352. Roll axis 302 and insertion axis 352 form the legs of the triangle, and linear axis 306 extends between first pitch axis 304 and second pitch axis 308 to insertion axis 352 to form a hypotenuse of the triangle. A length of the hypotenuse can be changed by moving the sublinks of prismatic link 218 at prismatic joint 230, e.g., by sliding prismatic joint 230 along linear axis 306 extending through first pitch joint 220 and second pitch joint 224. Similarly, the lengths of the legs change when an angle between insertion axis 352 and roll axis 302 is altered by moving the links at first pitch joint 220 and second pitch joint 224. The legs and the hypotenuse of the triangle exist within a plane that can rotate about roll axis 302. The triangle has a vertex where insertion axis 352 intersects roll axis 302. In an embodiment, the links of robotic arm 204 are controlled by movement of respective motors at first pitch joint 220, prismatic joint 230, and second pitch joint 224 to position the vertex at remote center of motion 216.

Tool drive 214 can include a carriage 356 to hold surgical tool 104 (FIGS. 7A-8B). As described below, carriage 356 is movable relative to tool guide 350 in a direction of insertion axis 352. More particularly, tool drive 214 can have a respective prismatic joint connecting carriage 356 to tool guide 350, and the prismatic joint can allow carriage 356 to move along insertion axis 352 toward or away from guide tube 354. A distal end or shaft of surgical tool 104 mounted on carriage 356 can therefore move parallel to the movement of carriage 356. While a location on guide tube 354, e.g., a location in the lumen of guide tube 354, is maintained at remote center of motion 216 based on software-controlled movement of the linkage joints about/along their respective axes of motion, the distal end and/or shaft of surgical tool 104 can be inserted or retracted through the lumen of guide tube 354. The distal end and/or shaft of surgical tool 104 can move through the access point in patient 102, which is collocated at remote center of motion 216. The tool feature can therefore pivot about remote center of motion 216.

Figure 4:
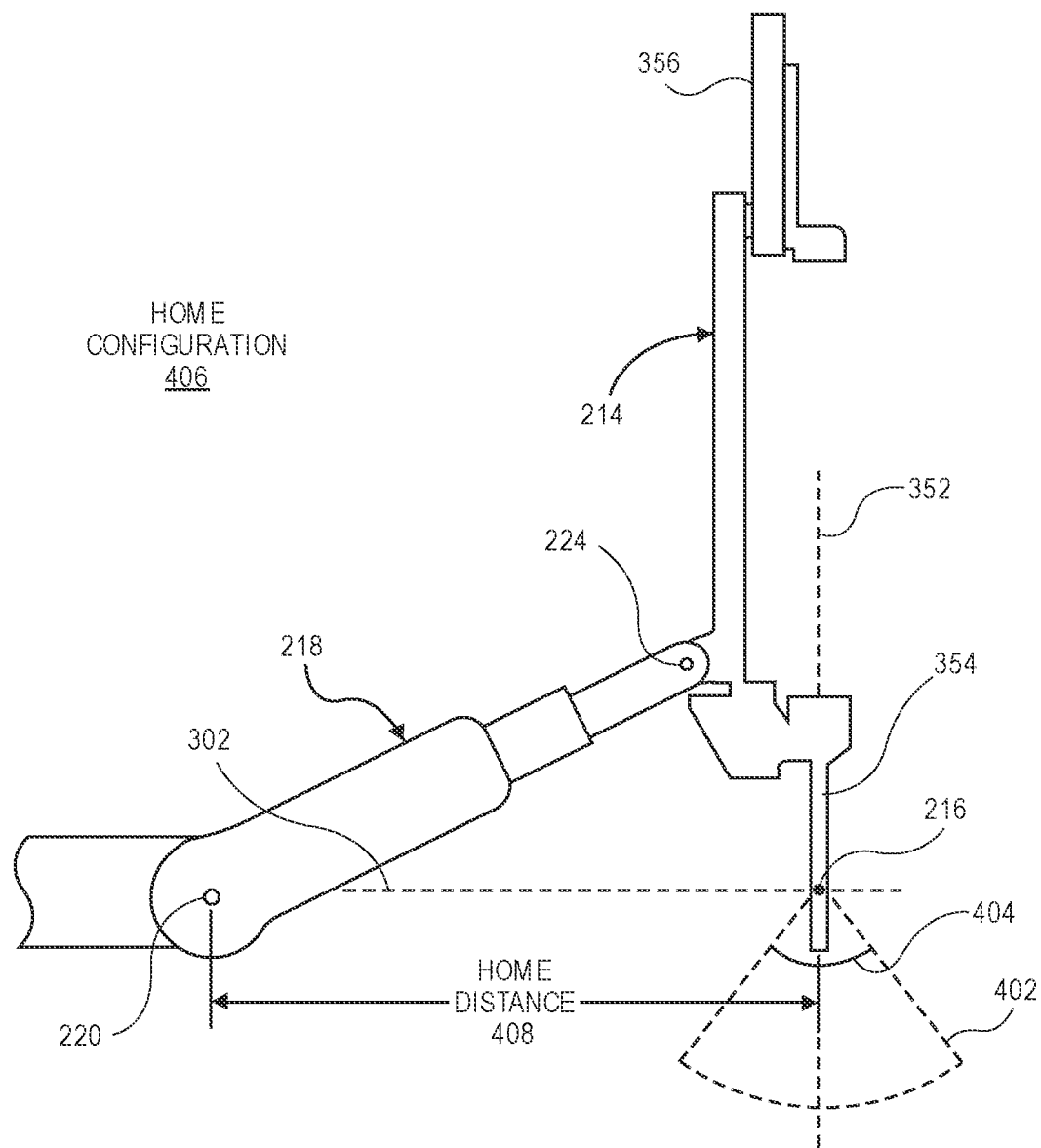
FIG. 4 is a side view of a robotic arm in a home configuration, in accordance with an embodiment.

Referring to FIG. 4, a side view of a robotic arm in a home configuration is shown in accordance with an embodiment. Robotic arm 204 can be moved continuously between numerous configurations or states by controlling the movement at the linkage joints. In an embodiment, movement of the linkage can be controlled such that remote center of motion 216 is maintained at a fixed point in space, and guide tube 354 pivots about the remote center of motion. It will be appreciated then, that a distal end of guide tube 354, e.g., below roll axis 302, and/or a distal end of surgical tool 104 can sweep through a conical workspace 402 as guide tube 354 pivots about remote center of motion 216. A swept working angle 404 of conical workspace 402 can depend on a length of the variable-length link, as described below. For example, an optimal link length may exist at which working angle 404 is maximized. Similarly, a radius of conical workspace 402 can depend on a position of carriage 356 along insertion axis 352. For example, driving the distal end of surgical tool 104 in the distal direction along insertion axis 352 can increase the radius of conical workspace 402 below remote center of motion 216.

Robotic arm 204 can have several home configurations 406. The home configuration(s) may be defined as a linkage configuration in which roll axis 302 is orthogonal to insertion axis 352. In the home configuration 406, roll axis 302 can intersect insertion axis 352 at remote center of motion 216. The reference triangle defining the remote center of motion mechanism can be a right triangle in the home configuration(s). The reference triangles correspond to each home configuration can have different length hypotenuses depending on a length of prismatic link 218, and similarly, the reference triangle of each home configuration 406 can have a respective home distance 408 between first pitch joint 220 and remote center of motion 216 (home distance 408 being a length of a base leg of the reference triangle). For each home configuration 406 of robotic arm 204, first pitch joint 220, prismatic joint 230, and second pitch joint 224 of robotic arm 204 are movable to sweep the insertion axis 352 through a working angle 404 while maintaining surgical tool 104 and/or tool guide 350 at remote center of motion 216.

Working angle 404 represents the angular zone within which robotic arm 112 can maintain tool guide 350 at remote center of motion 216. Outside of this range, one or more joints of the remote center of motion mechanism may be unable to continue motion, and thus, further adjustment of tool guide 350 to coincide with remote center of motion 216 may be impossible. For example, prismatic joint 230 and/or second pitch joint 224 may be at an end of a range of motion in a first direction (FIG. 5) or at an end of a range of motion in an opposite direction (FIG. 6). Accordingly, if motion is continued at first pitch joint 220 in either case, the location on tool guide 350 would pivot about first pitch joint 220 and move away from remote center of motion 216.

Figure 5:
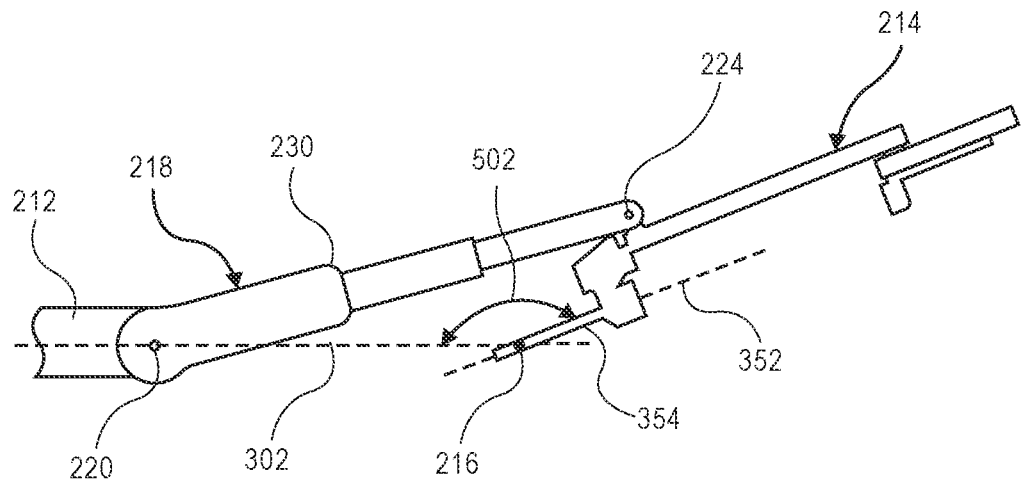
FIG. 5 is a side view of a robotic arm in a forward-pitched configuration, in accordance with an embodiment.
Figure 6:
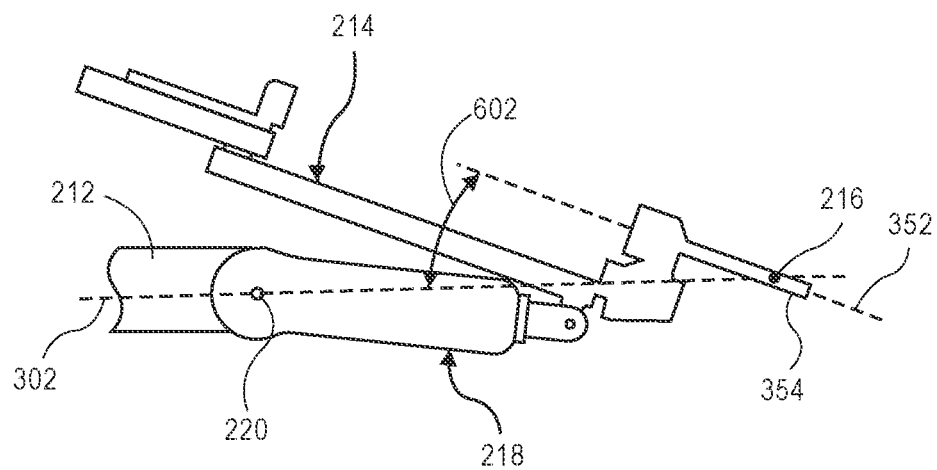
FIG. 6 is a side view of a robotic arm in a backward-pitched configuration, in accordance with an embodiment.

Referring to FIG. 5, a side view of a robotic arm in a forward-pitched configuration is shown in accordance with an embodiment. Insertion axis 352 can be pitched forward to pivot guide tube 354 about remote center of motion 216. The pitching motion of tool guide 350 can occur by actuating simultaneous motion at one or more of first pitch joint 220, second pitch joint 224, or prismatic joint 230. More particularly, prismatic link 218 can be lengthened while simultaneously increasing an angle 502 (in a clockwise direction) between insertion axis 352 and roll axis 302 to maintain a same location on guide tube 354 at remote center of motion 216. As tool guide 350 pitches forward, a range of motion is subtended. The range of motion can be within angle 502 between roll axis 302 and insertion axis 352 extending through remote center of motion 216. A vertical axis (not shown) that extends orthogonal to roll axis 302 can be used as a reference geometry. The vertical axis can be collinear with insertion axis 352 in the home configuration 406. In the forward-pitched configuration, a forward working subangle can be formed between the vertical axis and the insertion axis 352. The forward working subangle can define a portion of conical workspace 402. More particularly, the forward working subangle can define a portion of conical workspace 402 on a first side of a plane that contains the vertical axis reference geometry and is orthogonal to the page.

Referring to FIG. 6, a side view of a robotic arm in a backward-pitched configuration is shown in accordance with an embodiment. Insertion axis 352 can be pitched backward to pivot guide tube 354 about remote center of motion 216. More particularly, prismatic link 218 can be shortened while simultaneously decreasing the angle 602 between insertion axis 352 and roll axis 302, from angle 502, to maintain a same location on guide tube 354 at remote center of motion 216. As surgical tool 104 and/or tool guide 350 pitches backward, a difference between the angle 502 in FIG. 5 and the angle 602 in FIG. 6 can define a working angle 404 of conical workspace 402. In the backward-pitched configuration, a backward working subangle can be formed between the vertical axis and insertion axis 352. The backward working subangle can define a portion of conical workspace 402 on an opposite side of the workspace portion defined by the forward working subangle.

For each home configuration 406 of robotic arm 204, the working angle 404 swept by insertion axis 352 may be based on the respective home distance 408 of the home configuration 406. For a given home distance 408, insertion axis 352 will have a particular range of motion relative to roll axis 302. The range of motion can include the pitching motion through the forward working subangle of FIG. 5 and the backward working subangle of FIG. 6. For one home configuration 406, the forward working subangle and the backward working subangle are equal. For that home configuration, an axis of symmetry of conical workspace 402 is coaxial with the vertical axis reference geometry. Working angle 404 can be at a maximum in the symmetrical home configuration. For other home configurations, the forward working subangle and the backward working subangle are not equal. For those home configurations 406, the axis of symmetry of conical workspace 402 is tilted relative to the vertical axis. By way of example, and as described below, as home distance 408 of home configuration 406 increases, the forward working subangle decreases and the backward working subangle increases. By contrast, as home distance 408 of a home configuration 406 decreases, the forward working subangle increases and the backward working subangle decreases. In other words, the forward working subangle may be inversely proportional to home distance 408 and the backward working subangle may be proportional to the home distance 408 for a given home configuration 406.

Several examples of home distance-based working angles 404, which have been designed, are described here by way of example and not limitation. The home configuration having symmetric forward and backward working subangles can have a home distance 408 of 425 mm. That is, for the home configuration, when insertion axis 352 is orthogonal to roll axis 302, remote center of motion 216 may be spaced apart from first pitch joint 220 by 425 mm. In the home configuration 406, roll axis 302 is orthogonal to both insertion axis 352 and the vertical axis reference geometry, and intersects both axes at remote center of motion 216. When tool drive 214 is pitched forward to a maximum angle at which the same location on tool guide 350 can be positioned at remote center of motion 216, i.e., to working angle 502 for the symmetric home configuration 406, insertion axis 352 can be separated from the vertical axis reference geometry by 70 degrees. Similarly, when tool drive 214 is pitched backward to a maximum angle at which the same location on tool guide 350 can be positioned at remote center of motion 216, i.e., to the backward working subangle of FIG. 6 for the home configuration 406, insertion axis 352 can be separated from the vertical axis reference geometry by −70 degrees.

An alternative home configuration 406 having asymmetric forward and backward working subangles can have a home distance 408 of 525 mm. That is, for the asymmetric home configuration 406, when insertion axis 352 is orthogonal to roll axis 302, remote center of motion 216 may be spaced apart from first pitch joint 220 by 525 mm. In the asymmetric home configuration 406, roll axis 302 is orthogonal to both insertion axis 352 and the vertical axis reference geometry, and intersects both axes at remote center of motion 216. When tool drive 214 is pitched forward to angle 502 for the asymmetric home configuration 406, insertion axis 352 can be separated from the vertical axis reference geometry by 30° (less than the full range of motion in the forward direction). By contrast, when tool drive 214 is pitched backward to angle 602 for the alternative home configuration 406, insertion axis 352 can be separated from the vertical axis reference geometry by −70 degrees (the full range of motion in the backward direction).

Another asymmetric home configuration has an alternative home distance 408 of 325 mm. That is, for the asymmetric home configuration 406, when insertion axis 352 is orthogonal to roll axis 302, remote center of motion 216 may be spaced apart from first pitch joint 220 by 325 mm. When surgical tool 104 and/or tool drive 214 is pitched forward to the forward working angle 502 for the asymmetric home configuration 406, insertion axis 352 can be separated from the vertical axis reference geometry by 70 degrees (the full range of motion in the forward direction). By contrast, when surgical tool 104 and/or tool drive 214 is pitched backward to the backward working angle 602 for the asymmetric home configuration 406, insertion axis 352 can be separated from the vertical axis reference geometry by −5 degrees (less than the full range of motion in the backward direction).

The examples above show that, in contrast to a hardware-constrained robotic arm having a fixed distance from an input joint to a remote center of motion 216, a software-controlled robotic arm provides the ability to vary home distance 408. Furthermore, by varying home distance 408, a range of motion of surgical tool 104 and/or tool guide 350 can be controlled. This allows the range of motion to be optimized for certain operating conditions. For example, by increasing home distance 408 and accordingly decreasing forward working angle 502, additional clearance may be provided between surgical tool 104 and/or tool drive 214, and patient 102 or bedside operator 106. The additional patient clearance can allow bedside operator 106 to work within the space around the access point of patient 102 with less risk of being hit by the robotic arm. Similarly, by decreasing home distance 408, surgical robotic arm 112 can be made smaller overall to avoid collisions with adjacent robotic arms. When it is necessary to maximize conical workspace 402, e.g., when a maximum range of motion within patient 102 is required by the surgical operation, home distance 408 can be changed to achieve the symmetric home configuration and corresponding maximized working subangles. Accordingly, as compared to hardware-constrained robotic arms, surgical robotic arm 112 described herein can be adapted to the needs of a particular surgical scenario.

Figure 7A:
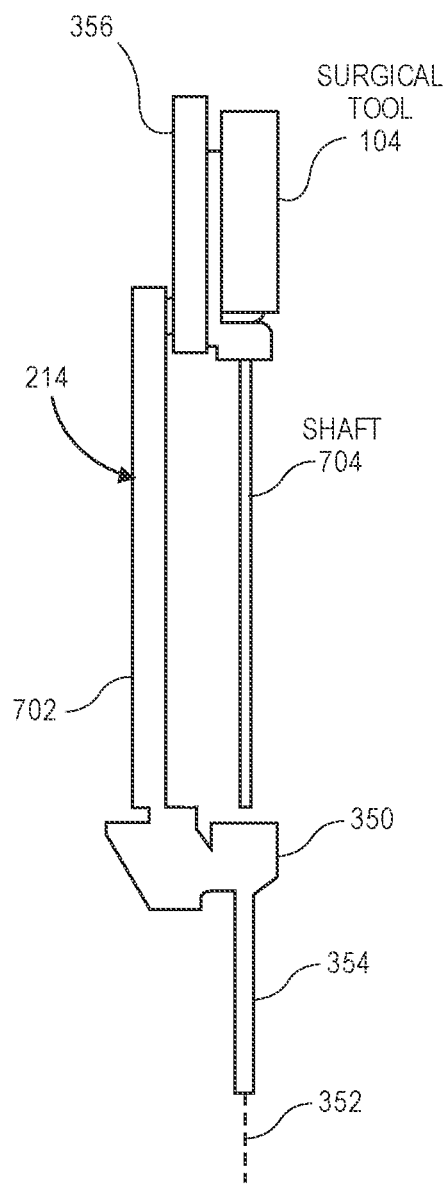
FIGS. 7A-7B are side views of a surgical tool mounted on a tool drive, in accordance with an embodiment.
Figure 7B:
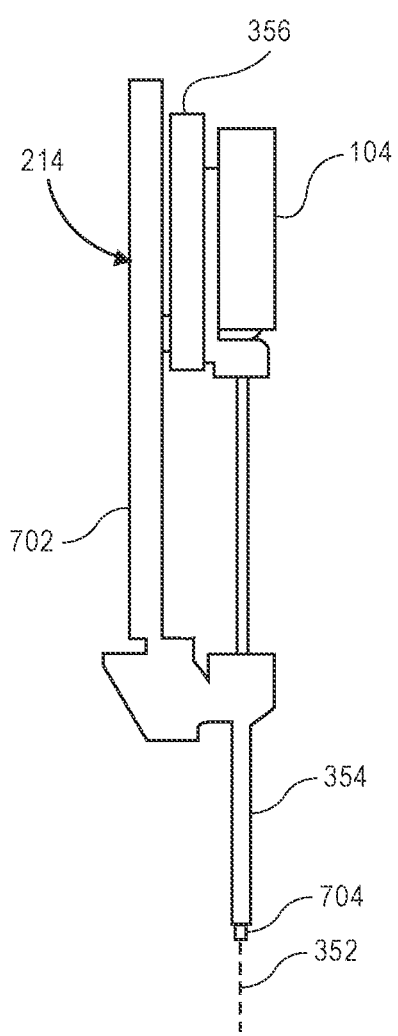

Referring to FIGS. 7A-7B, side views of a surgical tool mounted on a tool drive are shown in accordance with an embodiment. Tool drive 214 can move carriage 356 in a distal direction (toward guide tube 354) and a proximal direction (away from guide tube 354) along insertion axis 352. The linear motion can move surgical tool 104 from a fully retracted state to a fully inserted state at different positions along insertion axis 352.

FIG. 7A shows carriage 356 and surgical tool 104 in the fully retracted state. In an embodiment, tool drive 214 includes a guide base 702 fixed to the tool guide 350. For example, tool guide 350 can be mounted on guide base 702. By extension, guide tube 354 may have a consistent position in space relative to guide base 702. Carriage 356, on the other hand, may be movably coupled to guide base 702. For example, guide base 702 may include a linear-motion bearing, such as a stage, that is driven parallel to insertion axis 352 by a linear actuator, such as a motor-driven screw. Carriage 356 can be mounted directly on the linear-motion bearing to move relative to guide base 702 in the distal and proximal directions. Surgical tool 104 can be mounted on carriage 356 such that a shaft 704 of surgical tool 104 extends along insertion axis 352 in the distal direction. In the fully retracted state, shaft 704 may be held in the vertical space between carriage 356 and tool guide 350.

FIG. 7B shows carriage 356 and surgical tool 104 in the fully extended state. Carriage 356 and surgical tool 104 can be driven along insertion axis 352 distally relative to guide base 702. As carriage 356 is driven forward, shaft 704 of surgical tool 104 can enter the lumen of guide tube 354. Continued linear motion of carriage 356 can insert shaft 704 through guide tube 354 until a distal end of shaft 704 emerges. During surgery, the distal end of shaft 704 can include a camera, a grasper, or another end effector that may be used to perform a surgical operation within patient 102 when guide tube 354 is inserted within the surgical access point.

Figure 8A:
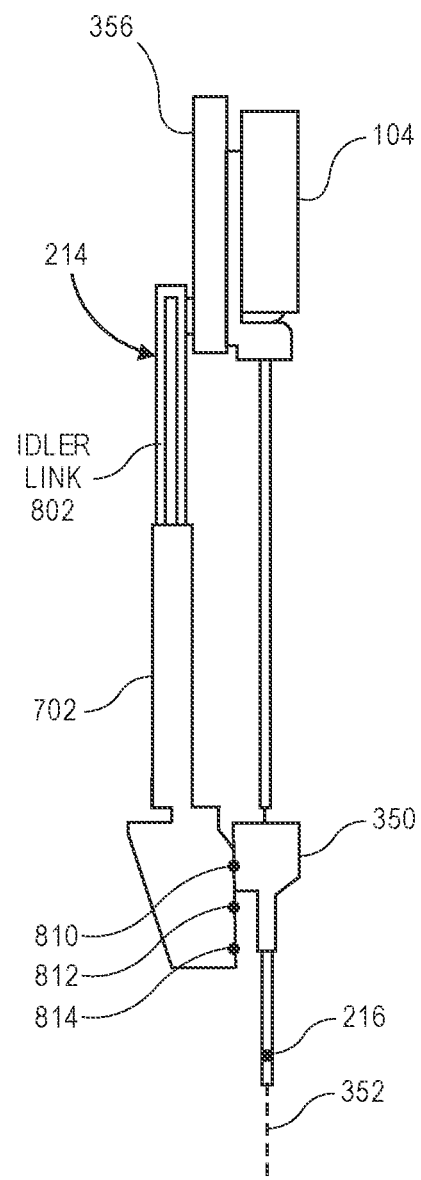
FIGS. 8A-8B are side views of a surgical tool mounted on a telescoping tool drive, in accordance with an embodiment.
Figure 8B:
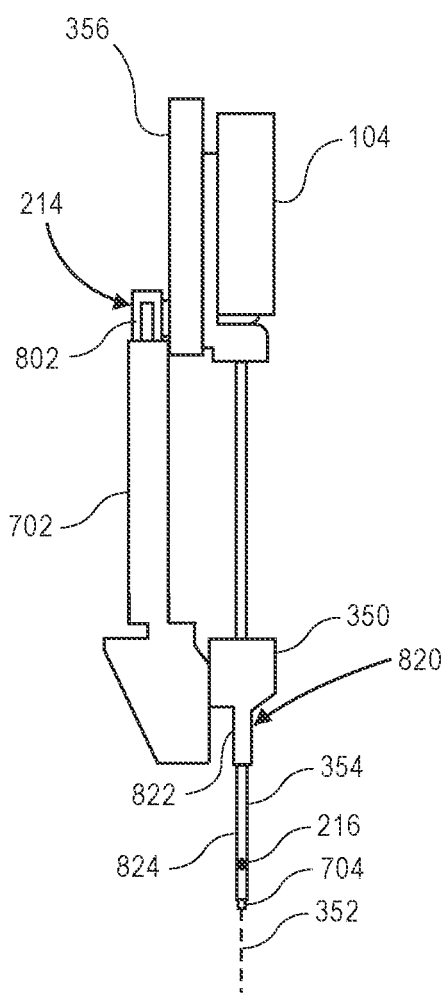

Referring to FIGS. 8A-8B, side views of a surgical tool mounted on a telescoping tool drive are shown in accordance with an embodiment. In an embodiment, tool drive 214 can include a prismatic joint having multiple stages. More particularly, like prismatic link 218, tool drive 214 can incorporate components that make movement of carriage 356 occur in a telescoping fashion.

FIG. 8A shows carriage 356 and surgical tool 104 in the fully retracted state. In an embodiment, guide base 702 is fixed to tool guide 350. Carriage 356, on the other hand, may be movably coupled to guide base 702. One or more idler link 802 can be connected to both guide base 702 and carriage 356, and idler link(s) 802 can simultaneously move relative to one or both of guide base 702 and carriage 356. The prismatic joint of tool drive 214 can include a mechanism for moving one or more of carriage 356 and tool base 702 in distal and proximal directions relative to idler link 802. For example, a first linear bearing may connect tool base 702 to idler link 802 and a first linear actuator can drive idler link 802 in a direction of motion defined by the bearing. Similarly, a second linear bearing may connect idler link 802 to carriage 356 and a second linear actuator (or a transmission element such as a belt) can drive carriage 356 in a direction of motion defined by the bearing. Accordingly, carriage 356 can move relative to tool base 702 in a telescoping fashion. In an embodiment, second pitch joint 224 can connect to idler link 802 such that guide base 702 can be driven forward and backward relative to the connection at second pitch joint 224 along idler link 802.

FIG. 8B shows carriage 356 and surgical tool 104 in the fully extended state. Carriage 356 and surgical tool 104 can be driven along insertion axis 352 distally relative to guide base 702. For example, idler link 802 can be driven distally relative to guide base 702 and/or carriage 356 can be driven distally relative to idler link 802. As carriage 356 is driven forward, shaft 704 of surgical tool 104 can enter the lumen of guide tube 354. Continued linear motion of carriage 356 can insert shaft 704 through guide tube 354 until a distal end of shaft 704 emerges within patient 102 to perform a surgical operation. In an embodiment, the telescoping action of tool drive 214 shown in FIGS. 8A-8B allows the overall envelope of tool drive 214 to be minimized. More particularly, the use of additional prismatic joint stages can allow tool drive 214 to fit within a smaller space in a compacted state. Accordingly, tool drive 214 having the telescoping prismatic joint 230 can be stowed under operating table 202.

In an embodiment, the range of motion of tool drive 214 can be increased by adjusting a clearance between tool drive 214 and patient 102. More particularly, the range of motion can be increased by one or more of moving a location at which tool drive 214 is coupled to the second pitch joint 224 along insertion axis 352, or incorporating a telescopic body in tool guide 350 to operatively telescope along insertion axis 352. It will be appreciated that these features can be incorporated into any of the embodiments described above, however, the features are only illustrated in FIGS. 8A-8B.

Referring again to FIG. 8A, a coupling position by which tool drive 214 is coupled to second pitch joint 224 (not shown) is operatively movable along insertion axis 352. In an embodiment, a mounting point at coupling position 810 can be movable along the tool drive stage, e.g., on tool guide base 702. For example, the tool guide base 702 can connect to the tool guide 350 at a proximal coupling position 810, and one or more of an intermediate coupling position 812, a distal coupling position 814, etc. The connection can be at various discrete locations, e.g., through respective couplings located at the coupling positions 810, 812, and 814 that individually connect to the tool guide 350. Alternatively, the tool guide base 702 and tool guide 350 can be mounted on moveable portions of a linear slide, and thus, can move relative to each other by actuating the slide. As the slide actuates, the tool guide 350 can move to points 810, 812, 814, etc., and thus, can change locations relative to tool guide base 702. Accordingly, the tool guide 350 can be unlatched and latched to discrete locations relative to the tool guide base 702, or moved continuously relative to the tool guide base 702, to change a distance between the tool drive 214 and patient 102. For example, when tool guide 350 is attached to tool guide base 702 at position 814, the tool drive is farther from patient 102. By making the mounting point of tool guide 350 movable along the tool drive stage, range of motion 502 can be increased.

Referring again to FIG. 8B, tool guide 350 includes a telescopic body 820 operatively telescoping along insertion axis 352. Telescopic body 820 can include a proximal guide tube 822 and a distal guide tube 824, by way of example, which are collinearly nested along insertion axis 352. In an embodiment, distal guide tube 824 can slide forward or backward within proximal guide tube 822 to make tool guide 350 telescopic. As telescoping body 820 is actuated, manually or automatically, a location of a distal end of distal guide tube 824 can change, and so can a location of remote center of motion 216 change relative to patient 102. As these points change, so may range of motion 502. For example, the guide tube can be extended to increase a clearance between tool guide base 702 and patient 102. Accordingly, range of motion 502 can be increased.

Figure 9:
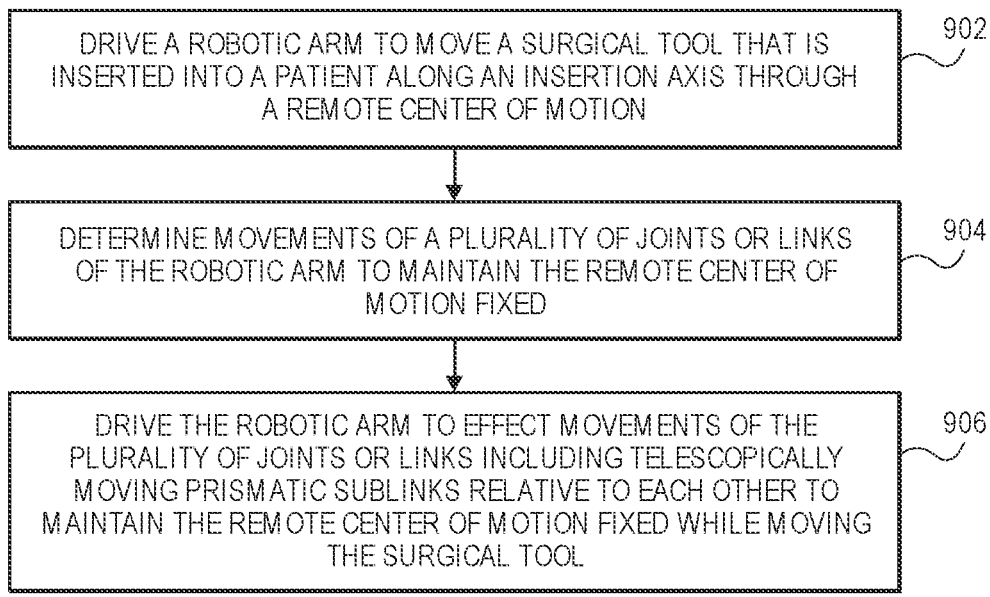
FIG. 9 is a flowchart of a method of controlling a robotic arm to maintain a remote center of motion fixed, in accordance with an embodiment.

Referring to FIG. 9, a flowchart of a method of controlling a robotic arm to maintain a remote center of motion fixed is shown in accordance with an embodiment. Robotic arm 204 can be positioned or moved to a first configuration. In the first configuration, roll axis 302 of roll joint 212 intersects insertion axis 352 of tool drive 214 at remote center of motion 216. Roll axis 302 is separated from insertion axis 352 in the first configuration by a first angle. For example, the first configuration can be a home configuration 406, and the first angle can be 90 degrees. Alternatively, the first configuration can be a state in which tool guide 350 is tilted relative to the vertical axis reference geometry, and thus, the first angle can be different than 90 degrees.

To move robotic arm 204 into the first configuration, motors at each joint of the linkage can be moved. For example, a stepper motor positioned at first pitch joint 220 can change an angle between linear axis 306 and roll axis 302. Similarly, a stepper motor positioned at second pitch joint 224 can change an angle between linear axis 306 and insertion axis 352. The angles set by the stepper motors can correspond to a length of prismatic link 218, as driven by a linear actuator connected to the links of prismatic link 218. The linear actuator that drives prismatic joint 230 of prismatic link 218 can include a lead screw. For example, in the case of a telescoping prismatic link 218, intermediate sublink 314 may include a linear-driven bearing that is moved by rotation of the lead screw. The other sublinks, e.g., the first sublink and the second sublink, may be connected to the intermediate sublink through a transmission mechanism, such as a belt and pulley mechanism. As the intermediate sublink is moved by rotation of the lead screw, the belt interconnecting the sublinks may also move to push and/or pull on the links. Accordingly, the sublinks can move in unison to change an overall length of prismatic link 218.

The position of the components of the remote center of motion mechanism may be sensed by one or more position sensors. For example, a network of absolute position sensors may be distributed throughout robotic arm 204 to detect movement and/or position of roll joint 212, prismatic link 218, and tool drive 214. In an embodiment, an absolute sensor is positioned in each joint of robotic arm 204, or in each joint of a portion of robotic arm 204 (such as the spherical arm) to detect the position of the joints. Feedback from the network of sensors can be received by a processor of surgical robotic system 100 (FIG. 10) and processed to determine the overall geometry of robotic arm 204. The processor can use the feedback to determine joint configurations that will keep remote center of motion 216 fixed. For example, remote center of motion 216 can be maintained fixed at the location on tool guide 350. The processor can generate drive signals that move actuators to achieve the desired geometry. For example, the processor generates drive signals to control movement of robotic arm 204 into the first configuration, or into a subsequent configuration, as described below. The movement between configurations can be performed while maintaining remote center of motion 216 fixed.

At operation 902, the processor can drive robotic arm 204 to move surgical tool 104 that is inserted into patient 102 along insertion axis 352 through remote center of motion 216. For example, the processor can drive robotic arm 204 to sweep insertion axis 352 through working angle 404. Insertion axis 352 can be swept through working angle 404 when surgical tool 104 and/or tool guide 350 is inserted into patient 102. Surgical tool 104 and/or tool guide 350 can be inserted into patient 102 along insertion axis 352 through remote center of motion 216.

At operation 904, the processor can determine movements of robotic arm 204, e.g., movements of the several joints or links of setup arm 250 and spherical arm 252 of robotic arm 204, to maintain remote center of motion 216 fixed. The processor can use feedback from the network of position sensors as inputs to a control algorithm used to control movement of robotic arm 204. For example, the spherical arm can be configured to be moved or guided under the control of the processor to maintain remote center of motion 216 fixed while sweeping insertion axis 352 through working angle 404.

At operation 906, the processor can drive robotic arm 204 to effect the movements, e.g., of the several joints or links of spherical arm 252, determined at operation 904. The components of robotic arm 204 can be repositioned to move robotic arm 204 into a second configuration. Repositioning of robotic arm 204 can include telescopically moving prismatic sublinks relative to each other. More particularly, the processor can control movement of prismatic link 218 such that several prismatic sublinks of the prismatic link 218 slide relative to each other. The linear actuator associated with prismatic joint 230 can be activated to slide first prismatic sublink 310 along linear axis 306 of prismatic joint 230 relative to second prismatic sublink 312. Sliding the prismatic sublinks can include sliding first prismatic sublink 310 relative to intermediate prismatic sublink 314 in a first direction along linear axis 306, and sliding second prismatic sublink 312 relative to intermediate prismatic sublink 314 in a second direction opposite to the first direction. More particularly, the sublinks can slide apart to increase an overall length of prismatic link 218. In any case, the prismatic sublinks can be moved relative to each by prismatic joint 230.

In the second configuration, roll axis 302 is separated from insertion axis 352 by a second angle. The second angle may be different than the first angle. In the second configuration, remote center of motion 216 can be in the same position as in the first configuration. Accordingly, movement from the first configuration to the second configuration is controlled by the processor to maintain remote center of motion 216 fixed while insertion axis 352 is swept through working angle 404.

In an embodiment, carriage 356 of tool drive 214 is moved in a direction of insertion axis 352. More particularly, carriage 356 can be moved relative to tool guide 350. For example, carriage 356 can be driven distally along insertion axis 352 to cause shaft 704 of surgical tool 104, which is mounted on carriage 356, to plunge through the lumen of guide tube 354 into patient 102.

Figure 10:
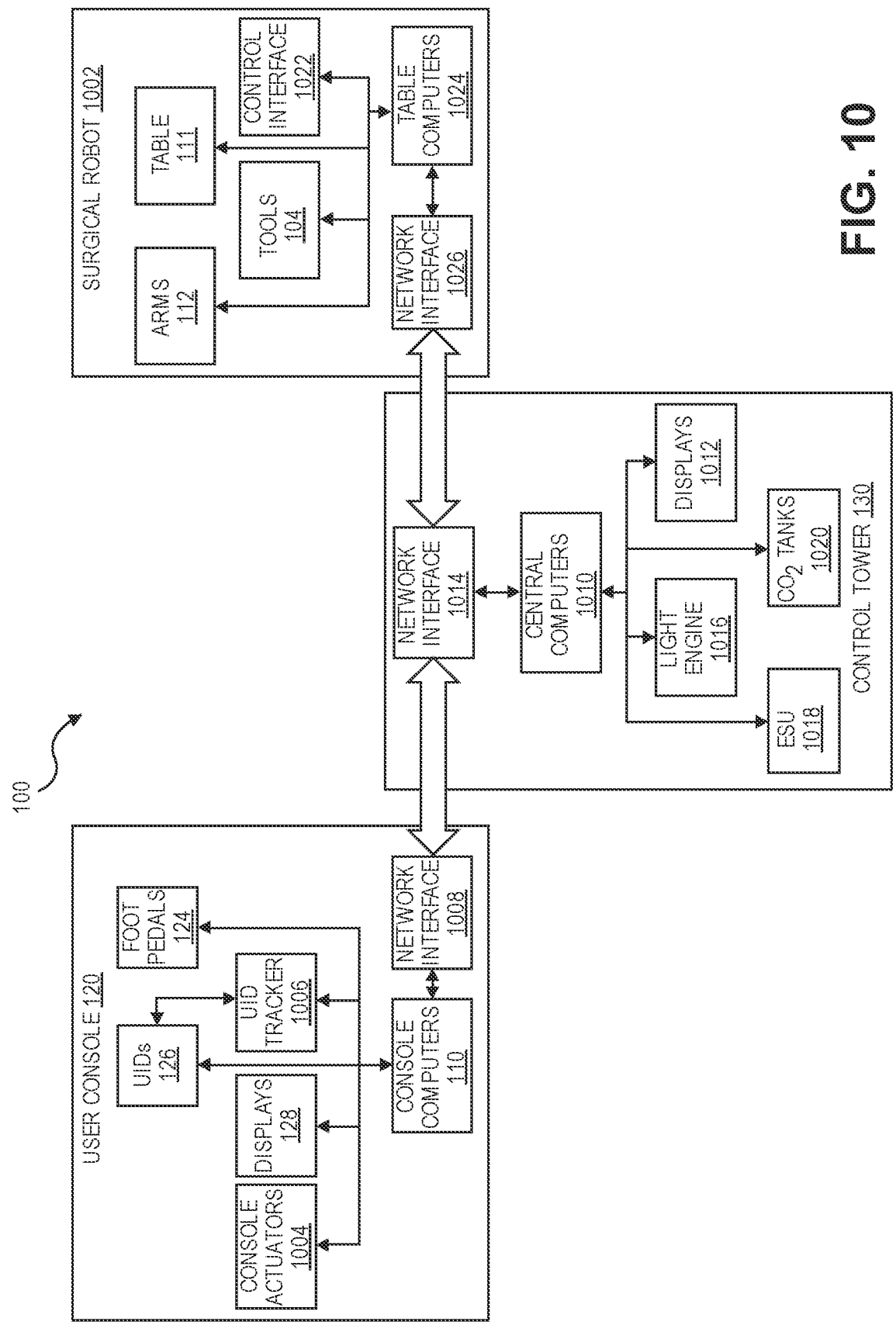
FIG. 10 is a block diagram of exemplary hardware components of a surgical robotic system, in accordance with an embodiment.

Referring to FIG. 10, a block diagram of exemplary hardware components of a surgical robotic system is shown in accordance with an embodiment. The exemplary surgical robotic system 100 may include a user console 120, a surgical robot 1002, and a control tower 130. The surgical robotic system 100 may include other additional hardware components; thus, the diagram is provided by way of example and not limitation to the system architecture.

As described above, the user console 120 comprises console computers 110 and one or more UIDs 126. User console 120 can include console actuators 1004, displays 128, a UID tracker 1006, foot pedals 124, and a network interface 1108. A user or surgeon sitting at the user console 120 can adjust ergonomic settings of the user console 120 manually, or the settings can be automatically adjusted according to the user profile or preference. The manual and automatic adjustments may be achieved through driving the console actuators 1004 based on user input or stored configurations by the console computers 110. The user may perform robot-assisted surgeries by controlling the surgical robot 1002 using two master UIDs 126 and foot pedals 124. Positions and orientations of the UIDs 126 are continuously tracked by the UID tracker 1006, and status changes are recorded by the console computers 110 as user input and dispatched to the control tower 130 via the network interface 1008. Real-time surgical video of patient anatomy, instrumentation, and relevant software apps can be presented to the user on the high resolution 3-D displays 128 including open or immersive displays.

Unlike other existing surgical robotic systems, the user console 120 disclosed herein may be communicatively coupled to the control tower 130 over a single fiber optic cable. The user console also provides additional features for improved ergonomics. For example, both an open and immersive display are offered compared to only an immersive display. Furthermore, a highly-adjustable seat for surgeons and master UIDs tracked through electromagnetic or optical trackers are included at the user console 120 for improved ergonomics. To improve safety, eye tracking, head tracking, and/or seat swivel tracking can be implemented to prevent accidental tool motion, for example, by pausing or locking teleoperation when the user's gaze is not engaged in the surgical site on the open display for over a predetermined period of time.

The control tower 130 can be a mobile point-of-care cart housing touchscreen displays, computers that control the surgeon's robotically-assisted manipulation of instruments, safety systems, graphical user interface (GUI), light source, and video and graphics computers. As shown in FIG. 10, the control tower 130 may comprise central computers 1010 including at least a visualization computer, a control computer, and an auxiliary computer, various displays 1012 including a team display and a nurse display, and a network interface 1014 coupling the control tower 130 to both the user console 120 and the surgical robot 1002. The control tower 130 may also house third-party devices, such as an advanced light engine 1016, an electrosurgical generator unit (ESU) 1018, and insufflator and $CO_2$ tanks 1020. The control tower 130 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 1002 comprises an articulated operating table 111 with a plurality of integrated arms 112 that can be positioned over the target patient anatomy. A suite of compatible tools 104 can be attached to or detached from the distal ends of the arms 112, enabling the surgeon to perform various surgical procedures. The surgical robot 1002 may also comprise control interface 1022 for manual control of the arms 112, table 111, and tools 104. The control interface can include items such as, but not limited to, remote controls, buttons, panels, and touchscreens. Other accessories such as trocars (sleeves, seal cartridge, and obturators) and drapes may also be needed to perform procedures with the system. In some variations the plurality of arms 112 include forearms mounted on both sides of the operating table 111, with two arms on each side. For certain surgical procedures, an arm mounted on one side of the table can be positioned on the other side of the table by stretching out and crossing over under the table and arms mounted on the other side, resulting in a total of three arms positioned on the same side of the table 111. The surgical robot 1002 can also comprise table computers 1024 and a network interface 1026, which can place the surgical robot 1002 in communication with the control tower 130.

Robotic arm 204 can be described in other terms. Robotic arm 204 can be a multi-degree of freedom arm that has redundancy built into the arm geometry to enable several control modes that can maximize patient clearance, minimize forces applied to patient tissue by the arm, and minimize collisions between the arm and other structures, e.g., another arm, of the surgical robotic system 100. More particularly, the robotic arm 204 can maximize reach and access to patient 102 when robotic arm 204 is mounted on surgical robotic platform 111. The redundant control system can allow patient clearance, forces, and end effector control to be optimized.

The multi-degree of freedom arm 204 can include at least four mechanically independent distal degrees of freedom. For example, spherical arm 252 of robotic arm 204 may include the distal degrees of freedom, which can allow two intersecting rotational degrees of freedom around a remote center of motion 216. Additionally, a third distal linear degree of freedom can be provided, which intersects remote center of motion 216. These degrees of freedom provide the distal spherical mechanism of spherical arm 252. At least one of the rotational degrees of freedom in the distal spherical mechanism can contain a linear telescoping mechanism in conjunction with the two rotary joints. The combination can enable one of the rotations of surgical tool 104 around remote center of motion 216. The second rotational degree of freedom around remote center of motion 216 can be enabled by a rotary joint in combination with rotations of a remainder of joints of arm 204.

In an embodiment, the multi-degree of freedom arm can have at least five proximal degrees of freedom. For example, setup arm 250 of robotic arm 204 may include the proximal degrees of freedom, which can allow spherical arm 252 to be positioned with two additional degrees of redundancy. The redundant degrees of freedom can allow remote- or system-driven repositioning of the proximal body of the robotic arm 204 to extend the range of motion of spherical arm 252. Such repositioning can provide access to patient 102 while keeping surgical tool 104 in a same pose. Such repositioning can also avoid collisions between any portion of arm 204 and another arm of surgical robotic system 100 during surgery.

The multi-degree of freedom arm can include a linear stage with a carriage for a replaceable surgical tool 104. The linear stage can have a redundant linear degree of freedom. More particularly, the redundant linear degree of freedom can attach the linear stage to spherical arm 252 to allow a joint holding the linear stage to create more clearance between robotic arm 204 and a body of patient 102.

As described above, the multi-degree of freedom arm can have a degree of freedom that allows a position of the attachment of the pitch mechanism along the stage to be changed. More particularly, as described with respect to FIG. 8A, the attachment position 810 can be adjusted. Similarly, in an embodiment, the multi-degree of freedom arm can have a telescoping trocar that allows the trocar main body to be pulled aware from patient 102. For example, as is evident with respect to FIG. 8B, the telescoping trocar can be lengthened to create clearance between guide 702 and patient 102.

In addition to the physical mechanisms described above, robotic arm 204 can incorporate one or more sensors. In an embodiment, robotic arm 204 includes a skin sensor to detect a proximity to other components of surgical robotic system 100 or other objects in the operating arena. For example, a proximity to other arms, accessories, a body of patient 102, a body of user 106, etc., can be detected by the skin sensor.

Robotic arm 204 can incorporate one or more torque or force sensors in one or more of the joints or components of robotic arm 204. For example, a multi-degree of freedom sensor, which can sense force or torque, may be incorporated into a joint of the arm to detect force and/or torque applied to the joint during surgery. Similarly, a force or torque sensor can be integrated into tool guide 350, e.g., within the cannula of guide tube 354, to sense a force or torque applied during surgery.

Sensors of robotic arm 204 can include distance or position sensing sensors. For example, a position sensor can be mounted on tool guide 350, e.g., on the proximal or distal guide tubes, to detect or measure a distance from robotic arm 204 to patient 102. Similarly, optical sensors can be mounted at one or more locations on arm 204 to allow for tracking of a position of robotic arm 204 with respect to surgical table 111 and other objects within the operating arena.

The above-noted force and/or distance sensing sensors of robotic arm 204 can be used by surgical robotic system 100 to control robotic arm 204 according to several modes of operation. In a mode of operation, a position and orientation of the end effector of surgical tool 104 can be controlled based on readings taken by the sensors of robotic arm 204. In a mode of operation, a position of remote center of motion 216 can be controlled based on readings taken by the sensors of robotic arm 204. Similarly, in a mode of operation, a force on remote center of motion 216 can be controlled based on readings taken by the sensors of robotic arm 204.

The ability to sense forces on remote center of motion 216, tool guide 350, and other components of robotic arm 204 can allow, for example, a compliance of some of the parts of the arm that can collide with user 106 or patient 102 to be controlled. For example, the compliance of the stage can be controlled while maintaining a predetermined level of stiffness in remote center of motion 216.

In a mode of operation, the sensors of robotic arm 204 can provide distance or orientation readings to maximize a clearance between robotic arm 204 and patient 102. The maximized clearance can avoid collisions between the arm and the patient. Similarly, the position of arm 214 can be optimized to minimize collisions between: arm 214 and another arm of surgical robotic system 100, arm 214 and an accessory of surgical robotic system 100, arm 214 and patient 102, or arm 214 and operators 106.

The multi-degree of freedom arm can operate in additional modes of operation using the sensor data gathered from sensors incorporated in arms 250, 252 and/or tool drive 214. For example, in a mode of operation, arm 204 can allow for automatic trocar docking with a distal portion of arm 252, e.g., docking of tool guide 350 to the stage. The distal portion of arm 252 can be used to achieve fine docking motion, e.g., via operation of the mechanically independent distal degrees of freedom.

The proximal and distal degrees of freedom of the multi-degree of freedom arm can allow for movement of the arm components. For example, the two rotary degree-of-freedoms of spherical arm 252 allow for pitch/roll movement of the stage that can enable rotational movement of an end effector, e.g., surgical tool 104. Proximal joints of robotic arm, e.g., joints of setup arm 250, can be repositioned during operation whether spherical arm 252 is moving or not moving to reorient the workspace of spherical arm 252 with respect to patient 102.

In an embodiment, movement of the arm components can move remote center of motion 216 along roll axis 302. For example, the arm components can be adjusted to change a distance between remote center of motion 216 and first pitch joint 220 along roll axis 302.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A surgical robotic system for maintaining a remote center of motion fixed, comprising:
   an operating table;
   a surgical tool configured for insertion along an insertion axis into a patient through the remote center of motion; and
   a robotic arm mounted under the operating table, wherein the robotic arm includes
      a tool drive supporting the surgical tool, and
      a plurality of joints or links including
         a roll joint extending along a roll axis that intersects the insertion axis at the remote center of motion, and a prismatic link connecting the roll joint to the tool drive, wherein the prismatic link has a first end and a second end, extends along a linear axis from the first end to the second end, and includes a plurality of prismatic sublinks coupled by a prismatic joint between the roll joint and the tool drive, and wherein the linear axis is oblique to the roll axis and intersects the insertion axis;
      wherein the plurality of joints or links are configured to be moved or guided under the control of a processor including telescopically moving the prismatic sublinks relative to each other by the prismatic joint to maintain the remote center of motion fixed.

2. The surgical robotic system of claim 1, wherein a first pitch joint couples the prismatic link to the roll joint, wherein a second pitch joint couples the prismatic link to the tool drive, and wherein the prismatic joint slides along the linear axis extending through the first pitch joint and the second pitch joint.

3. The surgical robotic system of claim 2, wherein the prismatic link rotates relative to the roll joint at the first pitch joint, wherein the prismatic link rotates relative to the tool drive at the second pitch joint, and wherein the prismatic sublinks slide relative to each other along the linear axis.

4. The surgical robotic system of claim 1, wherein the robotic arm has a plurality of home configurations, each home configuration having a respective home distance between a first pitch joint and the remote center of motion when the roll axis is orthogonal to the insertion axis, wherein the first pitch joint, the prismatic joint, and a second pitch joint are movable to sweep the insertion axis through a working angle while maintaining the remote center of motion fixed, and wherein the working angle is based on the home distance.

5. The surgical robotic system of claim 1, wherein the prismatic sublinks include an intermediate prismatic sublink coupled to a first prismatic sublink and to a second prismatic sublink by the prismatic joint.

6. The surgical robotic system of claim 1, wherein the tool drive includes a carriage to hold a surgical tool, wherein a tool guide includes a guide tube having a lumen coaxial with the insertion axis to receive a shaft of the surgical tool, and wherein the carriage is movable relative to the tool guide in a direction of the insertion axis to insert the shaft through the lumen.

7. The surgical robotic system of claim 6, wherein the tool guide includes a telescopic body operatively telescoping along the insertion axis.

\* \* \* \* \*